United States Patent [19]

Saitoh et al.

[11] Patent Number: 4,901,729
[45] Date of Patent: Feb. 20, 1990

[54] ULTRASONIC PROBE HAVING ULTRASONIC PROPAGATION MEDIUM

[75] Inventors: Koetsu Saitoh, Tokyo; Masami Kawabuchi, Yokohama, both of Japan

[73] Assignee: Matsushita Electric Industrial Co., Ltd., Osaka, Japan

[21] Appl. No.: 166,339

[22] Filed: Mar. 10, 1988

[30] Foreign Application Priority Data

Mar. 10, 1987 [JP] Japan .................. 62-54555

[51] Int. Cl.⁴ ............................... A61B 8/00
[52] U.S. Cl. .................. 128/662.03; 310/336
[58] Field of Search ......... 128/662.03, 663.01, 128/661.01; 73/644; 310/328, 334–336, 340

[56] References Cited

U.S. PATENT DOCUMENTS

| | | | |
|---|---|---|---|
| 4,440,025 | 4/1984 | Hayakawa et al. | 73/644 X |
| 4,699,150 | 10/1987 | Kawabuchi et al. | 73/644 X |
| 4,760,738 | 8/1988 | Katamine | 73/644 |
| 4,769,571 | 9/1988 | Hafegu Jr. et al. | 73/644 |

FOREIGN PATENT DOCUMENTS

| | | | |
|---|---|---|---|
| 0043158 | 1/1982 | European Pat. Off. | 128/662.03 |
| 0210723 | 2/1987 | European Pat. Off. | 128/662.03 |
| 0239999 | 10/1987 | European Pat. Off. | 128/662.03 |
| 58-7231 | 1/1983 | Japan | 128/662.03 |
| 2009563 | 6/1979 | United Kingdom | 128/662.03 |
| 1558718 | 1/1980 | United Kingdom | 128/662.03 |

OTHER PUBLICATIONS

"A study of ultrasonographic examination of thyroid disease by a simple small water bag made of silicone gum" by H. Katano et al; JSUM Proceedings, 1985, pp. 347 and 348.

Primary Examiner—Francis Jaworski
Attorney, Agent, or Firm—Pollock, VandeSande & Priddy

[57] ABSTRACT

An ultrasonic probe having an ultrasonic propagation medium (8) is used in medical ultrasonic diagnostic systems for examination and inspection of inside of an examining body (9) by transmitting and receiving ultrasonic signals. The ultrasonic probe comprises a body (1), and the ultrasonic propagation medium (8) made of rubber cross-linked by cross linking agent. The ultrasonic propagation medium (8) is interposed between the examining body (9) and a portion for transmitting and receiving ultrasonic waves of the body (1) of the ultrasonic probe when the ultrasonic propagation medium (8) is used.

5 Claims, 3 Drawing Sheets

ULTRASONIC PROBE HAVING ULTRASONIC PROPAGATION MEDIUM

BACKGROUND OF THE INVENTION

This invention relates to an ultrasonic probe having an ultrasonic propagation medium for use in medical ultrasonic diagnostic systems for examination and inspection within an examining body by transmitting and receiving ultrasonic signals.

Recently, an examination or inspection method using an ultrasonic propagation medium between an examining body or a human body and an ultrasonic probe which emits and receives ultrasonic signals has been applied to the field of medical ultrasonic diagnostic systems or the like.

Such ultrasonic probes using an ultrasonic propagatio medium are respectively disclosed in Japanese Laid-open Patent Application No. 58-7231 adn at "Pages 347 to 358 of a paper for the 46th lecture of the Ultrasonic Medical Society of Japan, 1985". Referring to FIGS. 1 and 2, the conventional ultrasonic probe utilizing such ultrasonic propagation medium will be described hereinbelow.

FIG. 1 is an illustration showing a trapezoidal scanning type of the ultrasonic probe, which can obtain a wide examining region in spite of a small contact area to an examining body. In FIG. 1, numeral 101 denotes an array of transducer elements, numeral 102 denotes an acoustic matching layer provided along the curved surface of the array 101 of the transducer elements, numeral 103 denotes an ultrasonic propagation medium arranged in front of the acoustic matching layer 102. Numeral 104 denotes lead wires respectively connected to the arrayed transducer elements, numeral 105 denotes cables which connect the ultrasonic probe to a body of an ultrasonic diagnostic apparatus (not shown), numeral 106 denotes an body being examined, numeal 107 denotes a transmission ultrasonic wave, numeral 108 denotes a reception ultrasonic wave, numeral 109 denotes an imagination origin, numeral 110 denotes a center of curvature of the arrayed transducer elements, and numeral 111 denotes an examining region.

The operation of the above-mentioned conventional example will be described hereinbelow.

As is apparent from this figure, the acoustic matching layer 102 and the array 101 of the transducer elements arranged in a convexed form are in plane contact with the examining body 106 such as the human body by means of the ultrasonic propagation medium 103 provided in front of the matching layer 102. Moreover, the ultrasonic propagation medium 103 can increase the scanning angle of the ultrasonic waves, namely, enlarge the examined region. The ultrasonic waves 107 transmitted, in order, from each of the transducer elements of the array 101 are deflected in the human dbody 106, since an acoustic velocity in the ultrasonic propagation medium 103 is lower than that in the human body 106. The deflected ultrasonic waves are reflected within the body 106, and are received by the same transducer element which has emitted the waves. As is apparent from FIG. 1, in the ultrasonic probe, the examining region 111 of the ultrasonic signals in the body 106 is of a sector corresponding to a part of a circle whose center is designated at a point 109. This is because the acoustic velocity in the ultrasonic propagation medium 103 is different from that in the human body 106.

Silicon rubber or the like is used as the above-mentioned ultrasonic propagation medium 103. Silicon rubber or the like has an acoustic impedance which is close to an acoustic impedance (about 1.5 to $1.6 \times 10^5 g/cm^2 \cdot sec$) of the humand body 106 and an acoustic velocity (about 1000 m/sec) which is slower than acoustic velocity (about 1540 m/sec) of the human body 106.

As described above, in this ultrasonic probe, the examining region 111 is enlarged, and the contact surface of the ultrasonic probe with the human body 106 becomes flat. Therefore, there are advantages that the adhesion is good and the operation is easy.

FIG. 2 is a cross-sectional view showing the other example of the conventional linear scanning type of the ultrasonic probe. In FIG. 2, numeral 201 denotes a case, numeral 202 denotes an array of transducer elements provided at the front portion of the case 201, numeral 203 denotes a backing member provided at the rear portion of the array 202 of transducer elements, numeral 204 denotes lead wires respectively connected to the arrayed transducer elements 202, and numeral 205 denotes a cable connected to a body of an ultrasonic diagnostic apparatus (not shown). Numeral 206 denotes a body being examined, numeral 207 denotes an ultrasonic propagation medium provided between the arrayed transducer elements 202 and the examined body 206. The ultrasonic propagation medium 207 comprises a flexible bag 208 made of silicon rubber or the like in which bag degassed water 209 is contained.

The operation of the above-mentioned conventional example will be described hereinbelow.

Each of the arrayed transducer elements generates ultrasonic waves in order, with pulse voltage transmitted from the body of the ultrasonic diagnostic apparatus through the cable 205 being applied. The resulting ultrasonic waves are emitted to the examined body 206 through the ultrasonic propagation medium 207. The ultrasonic waves reflected within the examined body 206 are received by the transducer element which emits the ultrasonic waves, and are changed to electrical signals. The electrical signals are sent to the body of the ultrasonic diagnostic apparatus through the cable 205, and are processed so as to display an ultrasonic image.

By providing the ultrasonic propagation medium 207 between the examined body 206 and the portion for transmitting and receiving the ultrasonic waves, it is possible that the resolving power of the ultrasonic image in the vicinity of the transmitting and receiving portion or the surface of the examined body 206 is improved. Moreover, even if the surface of the examined body 206 has irregularities, the ultrasonic propagation medium 207 can be placed in good contact with the examined body 206. Therefore, there is the advantage that it is easy to obtain the ultrasonic image.

However, in the former of the above-mentioned conventional examples, the ultrasonic attenuation coefficient of the silicon rubber used as the ultrasonic propagation medium 103 is as large as about 1.5 dB/mm at the frequency of 3.5 MHz. Moreover, as is apparent from FIG. 1, there is a difference in thickness between the center portion and both end portions of the ultrasonic propagation medium 103. Therefore, an extremely large sensitivity difference arises between the center portion and both end portions of the arrayed transducer elements due to the difference of the attenuation in silicon rubber, so that it is impossible to avoid deterioration of the ultrasonic image. As a reuslt, there is a problem that a sensitivity correcting circuit is indispensable so as to correct the sensitivity difference. On the other hand, in the latter of the above-mentioned conventional examples, the ultrasonic propagation medium 207 comprising the rubber-made bag 208 which contains the degassed water 209 is placed in contact with the examined body 206 through a gel (not shown) so as to carry out an ultrasonic diagnosis. However, since the silicon-made bag 208 has a high permeability of water, the degassed water 209 in the bag 208 vaprizes through the silicon rubber-made bag 208 as time proceeds. Therefore, each time the ultrasonic propagation medium 207 is used, the degassed water 209 must be injected in the bag 208. Moreover, since the bag 208 containing the degassed water 209 is arranged to be thin, this bag 208 is weak against physical impacts. As a result, there is a problem that the bag 208 is occasionally broken so that the degassed water 209 flows to the examined body 206.

SUMMARY OF THE INVENTION

The present invention has been developed in order to remove the above-mentioned drawbacks inherent to the conventional ultrasonic probe having an ultrasonic propagation medium.

It is, therefore, an object of the present invention to provide an ultrasonic probe having an ultrasonic propagation medium through which an ultrasonic image having a high sensivitiy and a high resolvign power can be obtained.

Another object of the present invention is to provide an ultrasonic probe having an ultrasonic propagation medium in which the contact of the ultrasonic probe with an examined body and an operability are improved.

In accordance with the present invention there is provided an ultrasonic probe assembly comprising: a body of an ultrasonic probe; and an ultrasonic propagation medium made of rubber containing cross linking agent, the ultrasonic propagation medium being attached to a portion for transmitting and receiving ultrasonic waves of the body of the ultrasonic probe.

In accordance with the present invention there is further provided an ultrasonic propagation medium comprising rubber mixed with cross linking agent and cross-linked.

BRIEF DESCRIPTION OF THE DRAWINGS

The objects and features of the present invention will become more readily apparent from the following detailed description of the preferred embodiments taken in conjunction with the accompanying drawings in which.

DETAILED DESCRIPTION OF THE INVENTION

Figure 3:
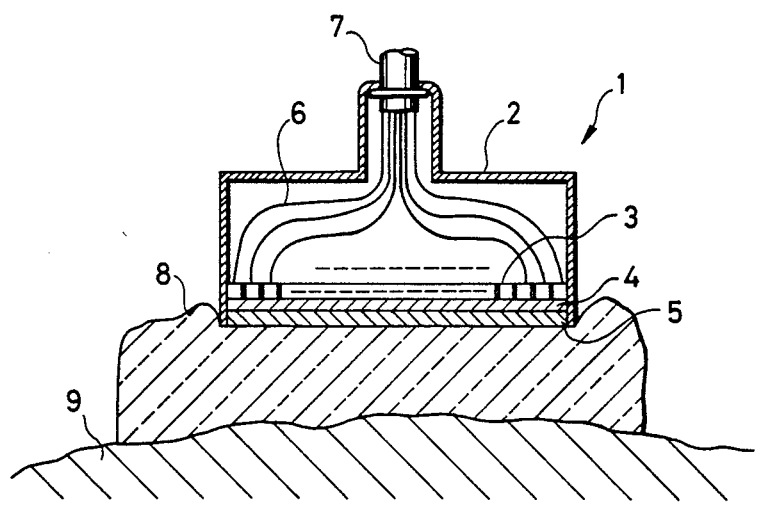
FIG. 3 is a cross-secitonal view showing an ultrasonic probe according to one of the embodiments of the present invention.

Referring now to the drawings, an embodiment of the present invention will be described hereinbelow. FIG. 3 is a cross-sectional view of an ultrasonic probe of one embodiment of the present invention.

Figure 2:
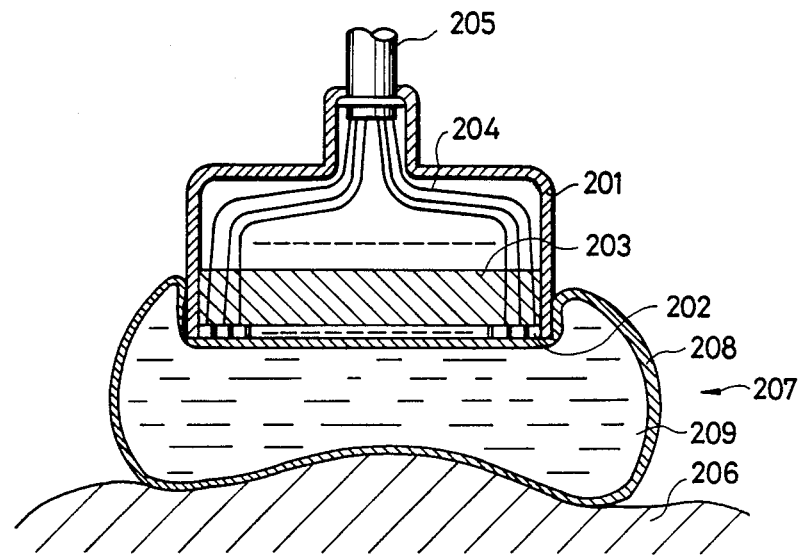

In FIG. 3, numeral 1 denotes a body of an ultrasonic probe, an array 3 of transducer elements is provided at the lower portion of the body, and the array 3 of the transducer elements has a number of slender plate-like transducer elements linearly successively arranged. An acoustic matching layer 4 having a single or multiple layers is provided on the surface of the array 3 of the transducer elements, and an acoustic lens 5 such as silicon rubber for focussing ultrasonic waves is provided on the front surface of the acoustic matching layer 4. Each of the transducer elements of the array 3 is connected to a body of an ultrasonic diagnostic apparatus (not shown) through lead wires 6 and a cable 7. In this embodiment, an ultrasonic propagation medium 8 is interposed between the acousti lens 5 and an examined body or a human body 9. The ultrasonic propagation medium 8 is arranged to be larger than the contact area of a portion for transmitting and receiving ultrasonic waves of the body 1 of the ultrasonic probe so that the contact area of the portion is fully covered with the medium 8. The thickness of the medium 8 is about 1 to 2 cm for application to a generally flat surface of the examined body 9. In other words, thicker medium 8 may be used for extremely undulatory surfaces of the examined body 9. The acoustic matching layer 4 and the acoustic lens 5 are conventionally used because the acoustic matching layer 4 can transmit ultrasonic waves efficiently and the acoustic lens 5 can focus ultrasonic waves to improve a resolving power, but are not shown in FIG. 2 for simplicity. In this embodiment, the ultrasonic probe having the ultrasonic propagation medium 8 satisfactorily operates irrespective of the presence of the acoustic matching layer 4 and the acoustic lens 5. This ultrasonic propagation medium 8 is made of rubber such as butadiene rubber which is cross linked by added peroxide. An acoustic impedance of such ultrasonic propagation medium 8 is close to that of the examined body 9, and an ultrsonic attenuation coefficient of the medium 8 is extremely small.

The operation of the above-mentioned embodiment will be described hereinbelow. Each of the arrayed transducer elements generates ultrasonic waves in order, with pulse voltage transmitted from the body of the ultrasonic diagnostic apparatus through the cable 7 being applied. The resulting ultrasonic waves are emitted to the examined body 9 through the acoustic matching layer 4, the acoustic lens 5, and the ultrasonic propagation medium 8. The ultrasonic waves reflected within the examined body 9 are received by the same transducer element which emits the ultrasonic waves, and are converted into electrical signals. The electrical signals are sent to the body of the ultrasonic diagnostic apparatus through the cable 7, and are processed so as to display an ultrasonic image.

Now the components of the ultrasonic propagation medium 8 will be described. First of all, an example using butadiene rubber cross-linked by dicumyl peroxide cross-linked agent will be described. This dicumyl peroxide cross-linked agent is a mixture of 40 parts of dicumyl peroxide used as a main component and 60 parts of calcium carbonate by weight, and is known as KAYAKUMIRU.D-40C produced by Kayaku-Nuri Co., Ltd. one hundred parts of butadiene rubber are mixed by 1.7 parts of dicumyl peroxide cross-linking agent (i.e. 0.68 parts of pure dicumyl peroxide) by weight, and the mixture is cross-linked under conditions of a temperature of about 170° C. and a time of about 15 min. The acoustic impedance (about $1.44 \times 10^5 \text{g/cm}^2 \cdot \text{sec}$) of the resulting ultrasonic propagation medium 8 is close to that of the examined body 9. Moreover, the acoustic velocity (1570 m/sec) in the ultrasonic propagation medium 8 is also close to that in the examined body 9. Besides, at a frequency of 3.5 MHz, the ultrasonic attenuation coefficient is 0.18 dB/mm. This value is about 1/10 of that of silicon rubber which is 1.5 dB/mm.

Figure 4:
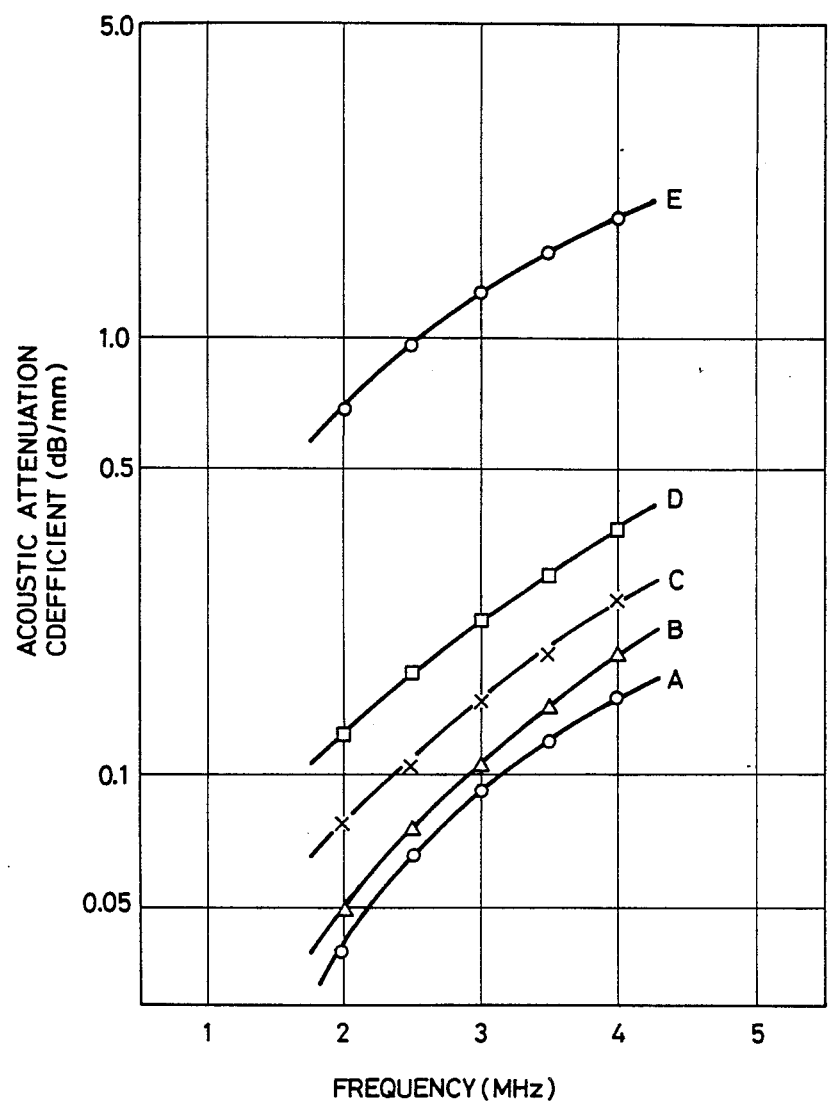
FIG. 4 is a graphic illustration for describing ultrasonic attenuation coefficients with respect to ultrasonic propagation media according to the present invention and comparative examples.

FIG. 4 is a graph showing the variation of the ultrasonic attenuation coefficient when varying the amount of dicumyl peroxide cross linking agent which is added to butadiene rubber. In FIG. 4, curves from A to C are obtained by mixtures and treatment thereof as follows.

| Composition of Mixtures | |
|---|---|
| parts of dicumyl peroxide cross linking agent by weight (to 100 parts of butadiene rubber) | parts of pure dicumyl peroxide by weight (to 100 parts of butadiene rubber) |
| A  0.2 | 0.08 |
| B  0.85 | 0.34 |
| C  1.7 | 0.68 |

The mixtures are cross-linked under conditions of a temperature of about 170° C. and a time of about 15 min. As is apparent from FIG. 4, ultrasonic attenuation coefficients decrease as the amounts of dicumyl peroxide cross linking agent is reduced. When seeing curve A where 0.2 parts of dicumyl peroxide cross-linking agent is added, the acoustic attenuation coefficient is 0.12 dB/mm at a frequency of 3.5 MHz, and the acoustic impedance ($1.44 \times 10^5 \text{g/cm}^2 \cdot \text{sec}$) is equal to that shown by curve C.

As comparative exmaples, the ultrasonic attenuation coefficient of the conventional silicon rubber, and the ultrasonic attenuation coefficient of vulcanized butadiene rubber in which 1.5 parts of sulfur are added to 100 parts of butadiene rubber by weight are respectively shown by curves E and D in FIG. 4. Silicon rubber shown by curve E has a large ultrasonic attenuation coefficient, and moreover, the ultrasonic attenuation coefficient of the sulfur-vulcanized butadiene rubber shown by curve D is about 0.3 dB/mm at 3.5 MHz so that the value is larger than those of butadiene rubbers cross-linked by dicumyl peroxide cross-linking agent.

On the other hand, the ultrasonic attenuation coefficient of butadiene rubber has a tendency to increase in accordance with the increment of the amount of dicumyl peroxide cross-linking agent. For example, in case that 3.4 parts of dicumyl peroxide cross-linking agent (i.e. 1.36 parts of pure dicumyl peroxide) are added to 100 parts of butadiene rubber by weight, the ultrasonic attenuation coefficient is 0.35 dB/mm at 3.5 MHz which value is larger than that of sulfur-vulcanized butadiene rubber (shown by D in FIG. 4). Moreover, in this case, the elasticity of the cross-linked butadiene rubber extremely decreases, and this rubber becomes fragile and crumbly so that this rubber cannot be used practically. The cross-linked butadiene rubber has a low ultrasonic attenuation coefficient, and can be used practically, when to 100 parts of rubber, the amount of dicumyl peroxide cross linking-agent is set less than 2 parts (i.e. 0.8 parts of pure dicumyl peroxide).

Figure 1:
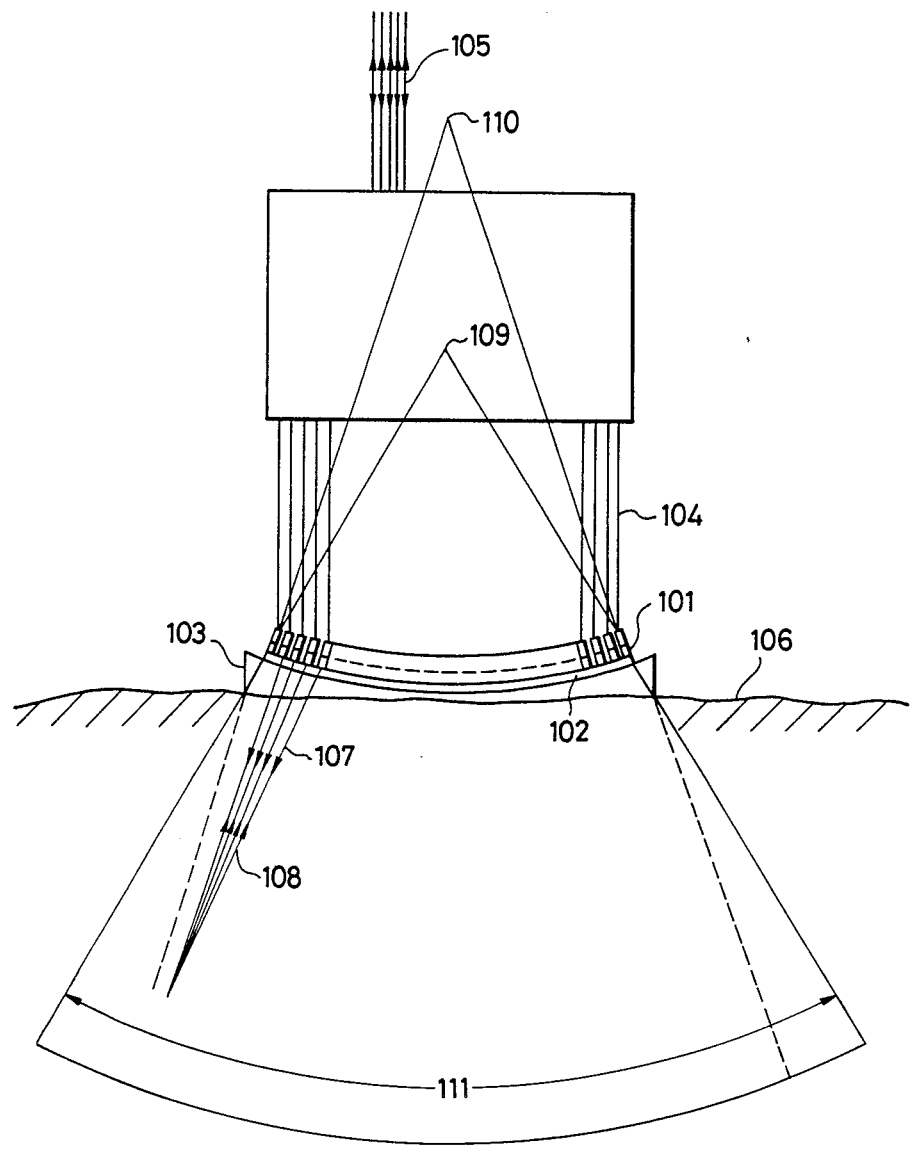
FIGS. 1 and 2 are an illustration and a cross-sectional view showing the conventional ultrasonic probes respectively.

Since the acoustic impedance of the above-mentioned ultrasonic propagation medium 8 is close to that of the examined body 9, there is no mismatching in the vicinity of the examined body 9, thereby preventing the deterioration of the resolving power of images due to multiple reflection. Moreover, the ultrasonic attenuation coefficient is about 1/10 of that of the conventional silicon rubber. Therefore, when the ultrasonic propagation medium 8 of the present invention is used in the trapezoidal scanning type of the ultrasonic probe shown in FIG. 1, the sensitivity variation throughout the entire examining region becomes extremely small. As described above, this sensitivity variation is caused by the difference of the thickness between the center portion where the ultrasaonic propagation medium 103 is thin and both end portions where the ultrasonic propagation medium 103 is thick. As a result, it is unnecessary to provide a sensitivity correcting circuit.

Butadiene-styrene rubber is used as a main component of the ultrasonic propagation medium 8 of the above-mentioned embodiment. However, natural rubber, isoprene rubber, butadiene-styrene rubber, ethylene-propylene rubber, and the like can also be used.

In place of dicumyl peroxide cross-linking agent used in the above-mentioned embodiment, benzoyl peroxide, 1,4 (or 1,3)-bis (t-butylperoxy isopropyl) benzene, 2,5-dimethyl-2,5-di (t-butylperoxy) hexane, 1,1-bis-t-butylperoxy-3,3,5-trimethyl cylcohexane, n-butyl-4,4-bis (t-butylperoxy) valerate, t-butylperoxy isopropylcarbonate, and the like can be also used.

Besides, in the ultrasonic propagation medium 8 of the above-mentioned embodiment, butadiene rubber is mixed by dicumyl peroxide cross-linking agent, and the resulting mixture is cross-linked. Moreover, carbon black, zinc oxide, titanium oxide, silicic anhydride, calcium silicate, colloidal cacium carbonate, or the like can be also added to the mixture of butadiene rubber and dicumyl peroxide cross-linking agent so as to bring the acoustic impedance of the ultrasonic propagation medium 8 close to the acoustic impedance of the examined body 9. For example, when to the mixture of 100 parts of butadiene rubber and 1.7 parts of dicumyl peroxide cross-linking agent, 28 parts of carbon black are mixed by weight, and are cross-linked, the acoustic impedance of the ultrasonic propagation medium 8 becomes $1.65 \times 10^5 \text{g/cm}^2 \cdot \text{sec}$ which value is substantially equal to the acoustic impedance (1.5 to $1.6 \times 10^5 \text{g/cm}^2 \cdot \text{sec}$) of the examined body 9. In this case, although the ultrasonic attenuation coefficient (0.3 to 0.4 dB/mm at MHz) slightly increases, this value is about 1/5 of that of the conventional silicon rubber so that the resulting ultrasonic propagation medium 8 can be used practically. As is apparent from the properties described above, the above-mentioned additives can be also used practically.

In the ultrasonic propagation medium 8, the desirable properaties are as follows:

(1) The acoustic impedance is close to the impedance (1.5 to $1.6 \times 10^5 \text{g/cm}^2 \cdot \text{sec}$) of the examined body 9.

(2) The ultrasonic attenuation coefficient is small.

(3) This medium 8 has a low hardness, and an easiness for handling so as to be placed in good contact with the examined body 9.

(4) This medium 8 has chemical stability.

The ultrasonic propagation medium 8 of this invention satisfies the properties of (1) and (2) as is apparent from the detailed description of the above. About the property (3), the desirable hardness of the medium 8 can be freely obtained by chanign the amount of the cross-linking agent. For example, when 2 parts of dicumyl peroxide cross-linking agent are added to 100 parts of butadiene rubber by weight, the hardness (shore hardness A) is about 50. On the other hand, when 0.5 parts of dicumyl peroxide cross-linking agent is added to 100 parts of butadiene rubber by weight, the hardness (shore hardness A) becomes about 30. Moreover, a gel-like medium 8 can be also obtained as well, by decreasing the amount of dicumyl peroxide cross-linking agent. Thus, the ultrasonic propagation medium 8 having a low hardness can be obtained freely so that the medium 8 is in good contact with the examined body 9. This medium 8 has a chemical stability so that this medium 8 is stable to water or alcohol which is used very frequently and has no bad effects on the examined body 9.

In this embodiment of the present invention, the ultrasonic propagation medium 8 comprising the cross-linked rubber is interposed between the examined body 9 and the surface of the portion for transmitting and receiving the ultrasonic waves. Therefore, it is unnecessary to inject degassed water into the rubber-made bag each time the bag is used as in the prior art. Moreover, there is no problem of wetting the examined body 9 with the bag being broken by physical impact. Besides, since the acoustic impedance of the medium 8 is close to that of the examined body 9, there is no multiple reflection in the vicinity of the boundary between the medium 8 and the examined body 9. And, since the ultrasonic attenuation coefficient is extremely small, the decrease of the sensitivity due to the use of the medium 8 is small. Moreover, since the ultrasonic propagation medium 8 is soft, the ultrasonic probe can be obtained which is palced in good contact with the examined body 9, has no deterioration of the properties, and has good operability.

In the above-mentioned embodiment, the linear type of the ultrasonic probe and the convex type of the ultrasonic probe have been described. Moreover, the ultrasonic propagation medium 8 can be applied to the duplex type or the like of the ultrasonic probe as well. The ultrasonic propagation medium 8 can be fixed to the surface of the portion for transmitting and receiving the ultrasonic waves of the body 1 of the ultrasonic probe by adhesions or the like, and can be detachably disposed to the bodies of the various types of the ultrasonic probes.

The above-described embodiments are just examples of the present invention, and therefore, it will be apparent to those skilled in the art that many modifications and variations may be made without departing from the scope of the present invention.

What is claimed is:
1. An ultrasonic probe assembly comprising:
  (a) a body of an ultrasonic probe having means for transmitting and receiving ultrasonic waves; and
  (b) an ultrasonic propagation medium attached to said means for transmitting and receiving, made of rubber containing a cross-linking agent, an amount of a main component of said cross-linking agent being less than 0.8 parts by weight, for 100 parts of said rubber.
2. An ultrasonic probe assembly as claimed in claim 1, wherein said rubber is at least one of natural rubber, isoprene rubber, butadiene-styrene rubber, ethylene-propylene rubber, and butadiene rubber.
3. An ultrasonic assembly as claimed in calim 1, wherein said cross linking agent is at least one of dicumyl peroxide, benzoyl peroxide, 1,4 (or 1,3)-bis (t-butyl-peroxy isopropyl) benzene, 2,5-dimethyl-2,5-di (t-butyl-peroxy) hexane, 1,1,-bis-t-butylperoxy-3,3,5-trimethyl cyclohexane, n-butyl-4,4-bis (t-butylperoxy) valerate, and t-butylperoxy isopropylcarbonate.
4. An ultrasonic probe assembly as claimed in claim 1, wherein said ultrasonic propagation medium is detachably connected to said body of said ultrasonic probe.
5. An ultrasonic probe assembly as claimed in claim 1, wherein a contact surface of said ultrasonic propagation medium is larger than a surface of said means for transmitting and receiving ultrasonic waves of said body of said ultrasonic probe, said in contact surface being contact with said surface of said portion.

* * * * *